US 7,771,430 B2

(12) United States Patent
Jones et al.

(10) Patent No.: US 7,771,430 B2
(45) Date of Patent: Aug. 10, 2010

(54) SINGLE ACTION ANTI-TORQUE ROD REDUCER

(75) Inventors: Scott A. Jones, McMurray, PA (US); Andy Rock, Spring Grove, PA (US)

(73) Assignee: K2M, Inc., Leesburg, VA (US)

( * ) Notice: Subject to any disclaimer, the term of this patent is extended or adjusted under 35 U.S.C. 154(b) by 287 days.

(21) Appl. No.: 11/514,915

(22) Filed: Sep. 5, 2006

(65) Prior Publication Data

US 2007/0093849 A1    Apr. 26, 2007

Related U.S. Application Data

(60) Provisional application No. 60/721,481, filed on Sep. 29, 2005.

(51) Int. Cl.
*A61F 5/00* (2006.01)
(52) U.S. Cl. ..................... 606/86 A; 606/279
(58) Field of Classification Search ............ 606/86, 606/279, 99, 104, 86 A, 103, 86 B
See application file for complete search history.

(56) References Cited

U.S. PATENT DOCUMENTS

| | | | | | |
|---|---|---|---|---|---|
| 2,248,054 | A | * | 7/1941 | Becker | 81/457 |
| 3,604,487 | A | * | 9/1971 | Gilbert | 81/443 |
| 5,020,519 | A | * | 6/1991 | Hayes et al. | 606/237 |
| 5,466,243 | A | * | 11/1995 | Schmieding et al. | 606/232 |
| 5,910,141 | A | | 6/1999 | Morrison et al. | |
| 6,416,521 | B1 | | 7/2002 | Waldner et al. | |
| 6,440,133 | B1 | * | 8/2002 | Beale et al. | 606/86 A |
| 6,648,888 | B1 | * | 11/2003 | Shluzas | 606/86 A |
| 6,660,006 | B2 | * | 12/2003 | Markworth et al. | 606/86 A |
| 6,790,209 | B2 | * | 9/2004 | Beale et al. | 606/86 A |
| 2003/0225408 | A1 | | 12/2003 | Nichols et al. | |
| 2004/0215190 | A1 | | 10/2004 | Nguyen et al. | |
| 2005/0143749 | A1 | * | 6/2005 | Zalenski et al. | 606/99 |
| 2005/0149053 | A1 | * | 7/2005 | Varieur et al. | 606/104 |
| 2005/0192587 | A1 | * | 9/2005 | Lim | 606/86 |
| 2005/0192589 | A1 | * | 9/2005 | Raymond et al. | 606/99 |
| 2005/0261702 | A1 | * | 11/2005 | Oribe et al. | 606/103 |
| 2006/0036260 | A1 | * | 2/2006 | Runco et al. | 606/99 |
| 2006/0074418 | A1 | * | 4/2006 | Jackson | 606/61 |
| 2006/0089651 | A1 | * | 4/2006 | Trudeau et al. | 606/86 |
| 2006/0200132 | A1 | * | 9/2006 | Chao et al. | 606/61 |
| 2007/0213722 | A1 | * | 9/2007 | Jones et al. | 606/61 |
| 2008/0172062 | A1 | * | 7/2008 | Donahue et al. | 606/104 |

OTHER PUBLICATIONS

International Search Report dated Mar. 15, 2007, issued in international application No. PCT/US06/34498, 4 pages.

* cited by examiner

*Primary Examiner*—Eduardo C Robert
*Assistant Examiner*—Devanie Dufour
(74) *Attorney, Agent, or Firm*—Carter DeLuca Farrell & Schmidt LLP

(57) ABSTRACT

Provided is a novel rod reducing device for use in spinal fixation procedures. The device is capable with a single action of securely grasping the head of a bone screw while reducing a connecting rod into the head of the bone screw and while in position on the bone screw provide a cannula access for a bone screw locking cap and tightening instrument and securing the bone screw during the tightening of the locking cap so as to provide an anti-torque effect. The device is also capable of releasing from the bone screw with a reversal of the single action used to activate the device. A method of using the device and a kit wherein the device is one component is also provided.

19 Claims, 8 Drawing Sheets

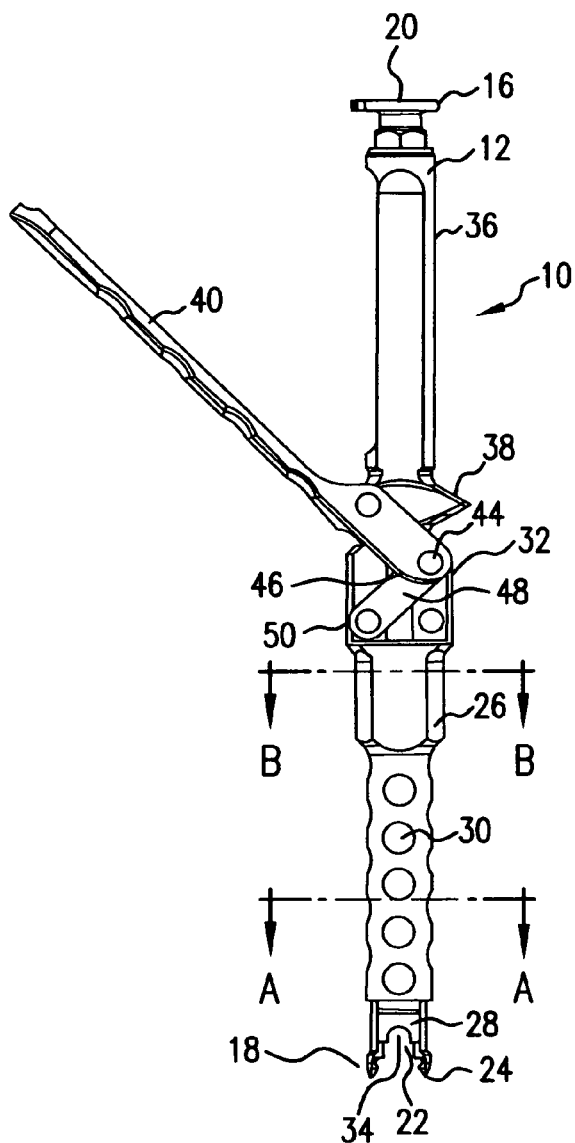
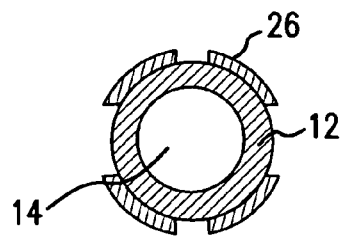
SECTION A-A
SCALE 2:1
FIG.6B
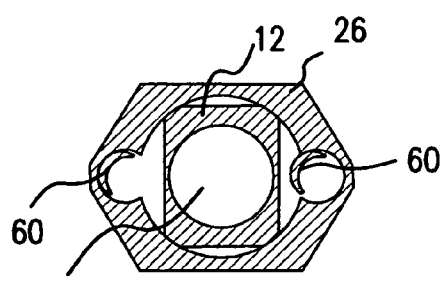
SECTION B-B
SCALE 2:1
FIG.6C
FIG.6A

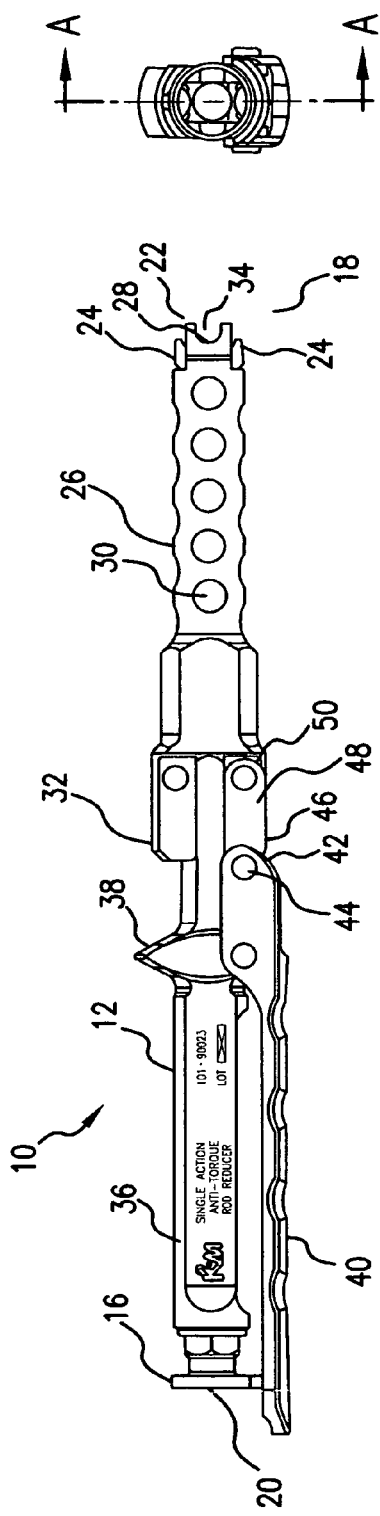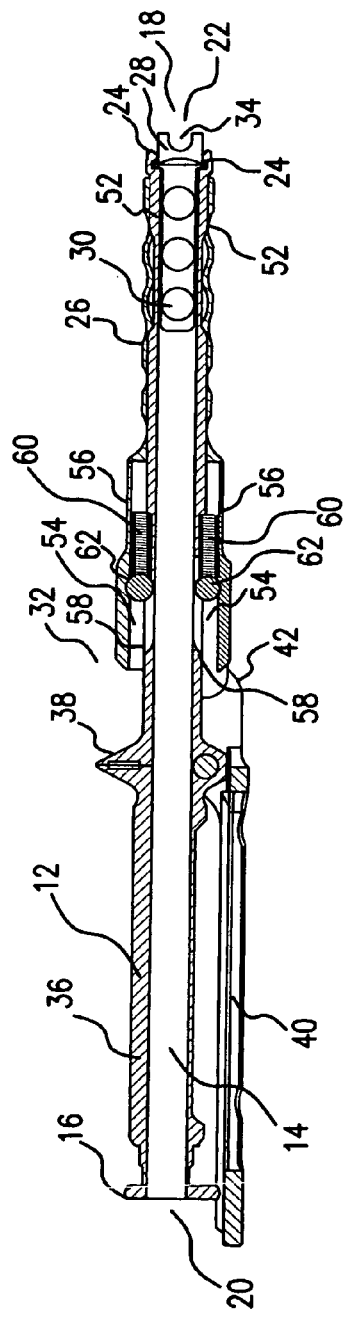
FIG. 7B
FIG. 7A
SECTION A-A
FIG. 7C

FIG.8D SECTION E-E SCALE 1:1

FIG.8C SECTION D-D SCALE 1:1

FIG.8B SECTION C-C SCALE 1:1

SINGLE ACTION ANTI-TORQUE ROD REDUCER

BACKGROUND

1. Technical Field

The present invention relates to orthopedic surgery, and in particular to devices for stabilizing and fixing the bones and joints of the body. Particularly, the present invention relates to an instrument capable of reducing a spinal rod into position in a rod receiving notch in the head of a bone screw and holding the same in position and providing anti-torque effect on the bone screw while a bone screw locking cap is attached to the head of the bone screw.

2. Background Art

The spinal column is a complex system of bones and connective tissues that provides support for the human body and protection for the spinal cord and nerves. The adult spine is comprised of 24 vertebral bodies, which are subdivided into three areas including seven cervical vertebrae, 12 thoracic vertebrae and five lumbar vertebrae. Between each vertebral body is an intervertebral disc that cushions and dampens the various translational and rotational forces exerted on the spinal column.

There are various disorders, diseases and types of injury which the spinal column may experience in a lifetime. The problems may include but are not limited to scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to eliminate motion at the intervertebral disc or joint. To achieve this, natural or artificial bone, along with a spacing device, replaces part or all of the intervertebral disc to form a rigid column of bone, which is stabilized by mechanical hardware.

The mechanical hardware used to immobilize the spinal column typically involves a series of bone screws and metal rods or plates. When the spine surgery is posteriorly performed, it is common practice to place bone screws into the vertebral bodies and then connect a metal rod between the bone screws thus creating a rigid structure between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of a bone screw and then securing that connecting rod in place often can require that the surgeon use a number of instruments and expend a great deal of time and effort to accomplish the task. When bone screws in several adjacent vertebra are to securely connected by a spinal rod, the repeated process of inserting the rod into the heads of the bone screws aid then securing the rod in place for each respective bone screw can be difficult, tiresome and time consuming. It is therefore important that an instrument be provided that is specifically designed to facilitate the process for the surgeon such that the connecting rod can be easily and quickly inserted into each bone screw and with minimal effort and loss of time. It is further important that the bone screws be held in a stable configuration to avoid the application of additional torque to the screw and the bone into which the screw is inserted when the locking cap is secured into position.

Conventional efforts to meet this need have fallen short in that no single instrument has been provided that effectively positions and inserts a connecting rod into position in the receiving slot of the head of a bone screw and also provides a stable anti-torque effect during the attachment of a bone screw locking cap to the head of each respective bone screw.

For these reasons there remains a need for a device which, in one simple action such as squeezing a lever, can reduce a posteriorly introduced rod into the head of a bone screw and provide an anti-torque effect to the bone screw while a bone screw locking cap is secured to the bone screw.

SUMMARY OF THE DISCLOSURE

The present system provides a novel instrument for use during spinal fixation surgery that with a single activation motion is capable of grasping the head of a bone screw while positioning a connecting rod into the rod receiving slot of that bone screw.

Also provided is an instrument that after insertion of a connecting rod into the receiving slot of a bone screw can then provide a stable anti-torque effect during the attachment of a bone screw locking cap.

Also provided is a cannulated instrument that securely connects to a bone screw and reduces a rod into position in the head of the bone screw with a single action and while connected to the bone screw provides an anti-torque effect while a bone screw locking cap positioned on and secured to the head of the bone screw through the cannulation of the device is attached.

Also provided is a method of connecting a rod to a bone screw, whereby the device holds the head of the bone screw in position while reducing the rod into position with a single action.

Also provided is a method of connecting a rod to a bone screw with a single action and then providing an anti-torque effect to the bone screw while a bone screw locking cap is attached to the head of the bone screw.

Also provided is a kit that can include at least one bone screw, at least one connecting rod, and a novel instrument for positioning the rod in each of the respective at least one bone screws and then providing an anti-torque effect during the attachment of a bone screw locking cap to each respective bone screw.

BRIEF DESCRIPTION OF THE DRAWINGS

The foregoing and other features of the disclosed embodiments will become apparent to one skilled in the art, relates upon consideration of the following description, with reference to the accompanying drawings, wherein:

FIGS. 6A-C show transverse cross-sectional views of the device in the open and unlocked configuration from a side view;

FIGS. 7A-D show the device in a closed and locked configuration; specifically shown in FIG. 7A is a side view of the device, in FIG. 7B is an end view of the device, in FIG. 7C is cross-section A-A of the device, and in FIG. 7D is a front view of the device.

FIGS. 8A-D show the device in the closed and locked configuration from a back view (FIG. 8A), a proximal cross-section (FIG. 8B), a mid-section cross-section of the same in FIG. 8C, and an extreme proximal cross-section the anti-torque connection point (FIG. 8D).

DETAILED DESCRIPTION OF PREFERRED EMBODIMENTS

Figure 1:
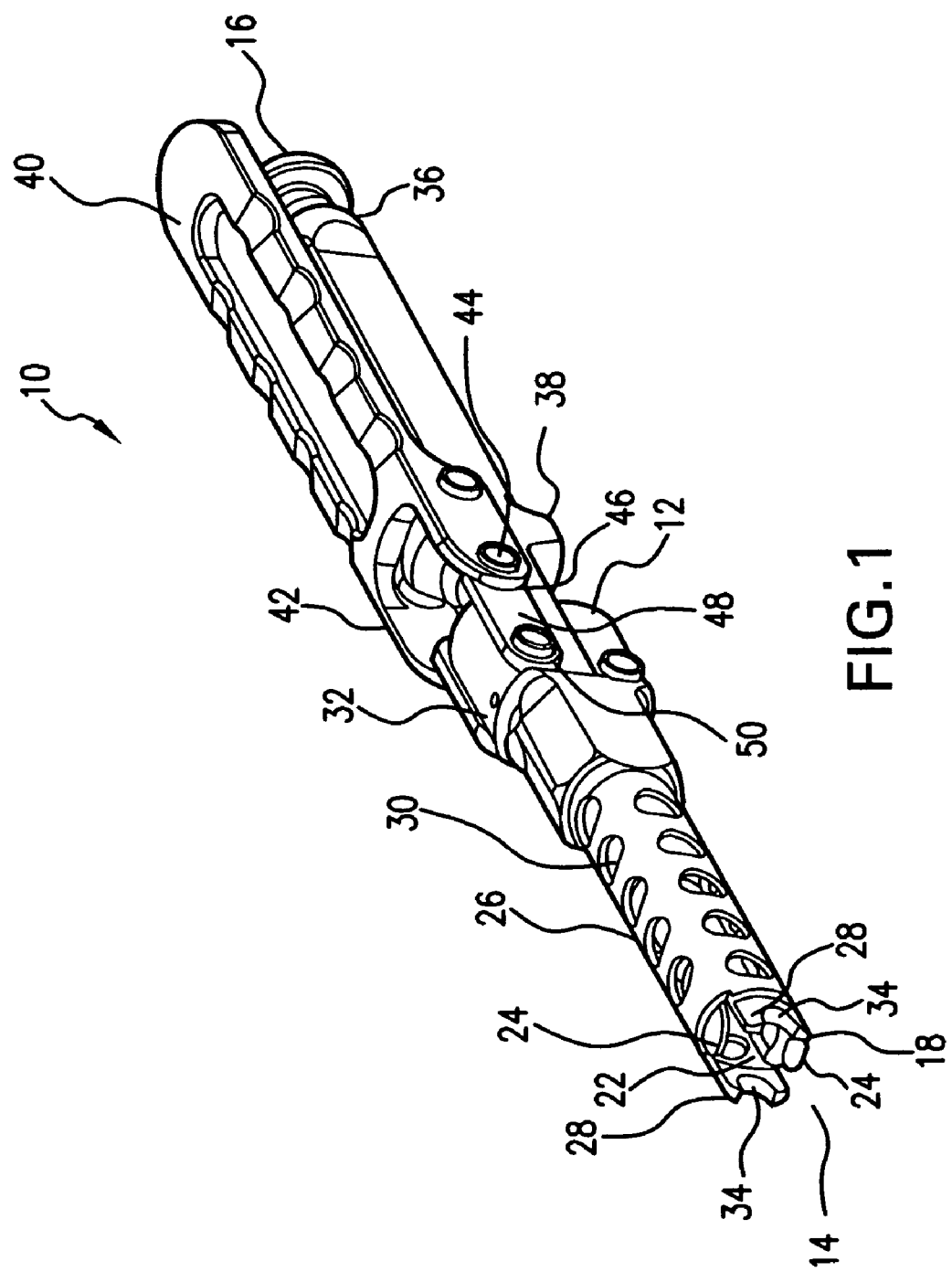
FIG. 1 shows an isometric view of the device.
Figure 2:
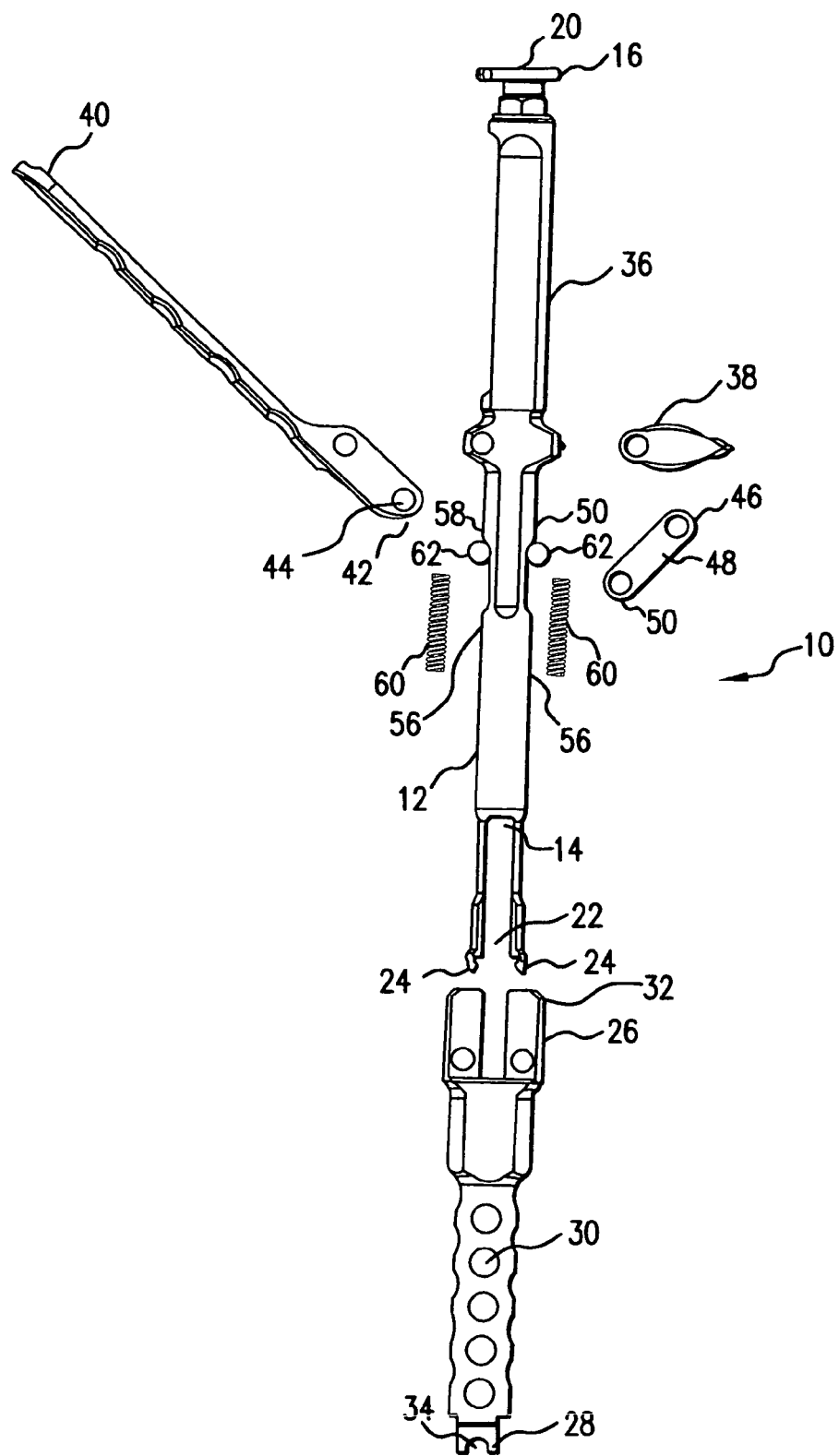
FIG. 2 is an exploded view showing the components of the device.
Figure 3A:
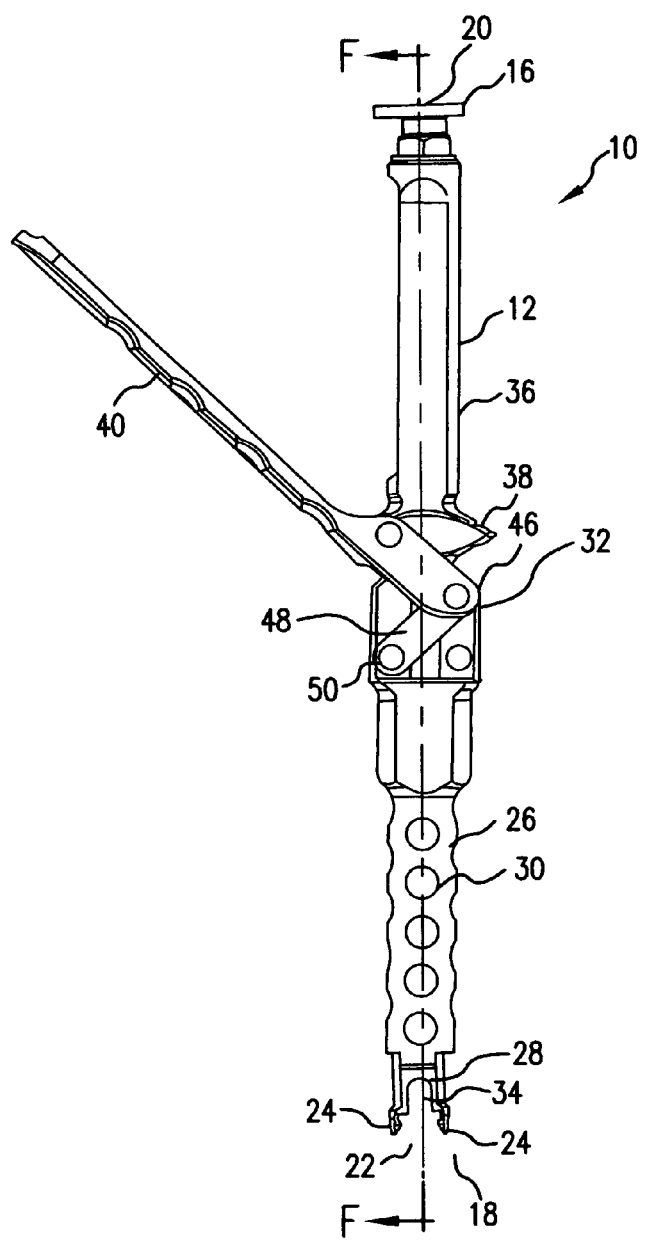
FIG. 3A-B show the device in the open and unlocked configuration from a side view as shown in FIG. 3A and a longitudinal cross-section of the same in FIG. 3B.
Figure 3B:
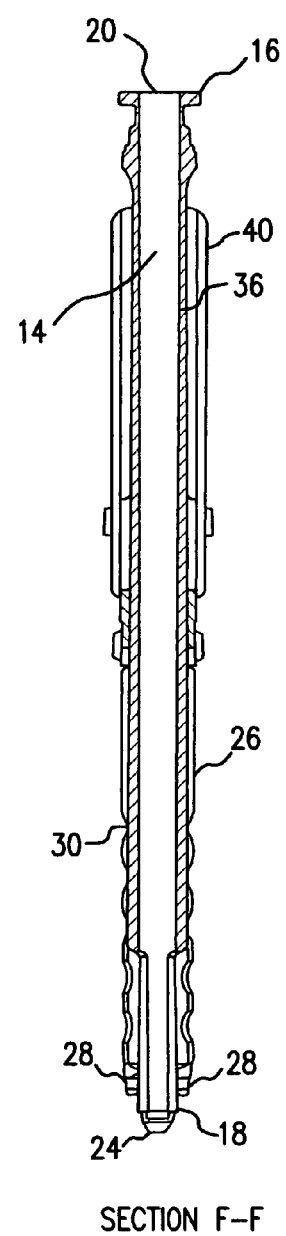
Figure 4:
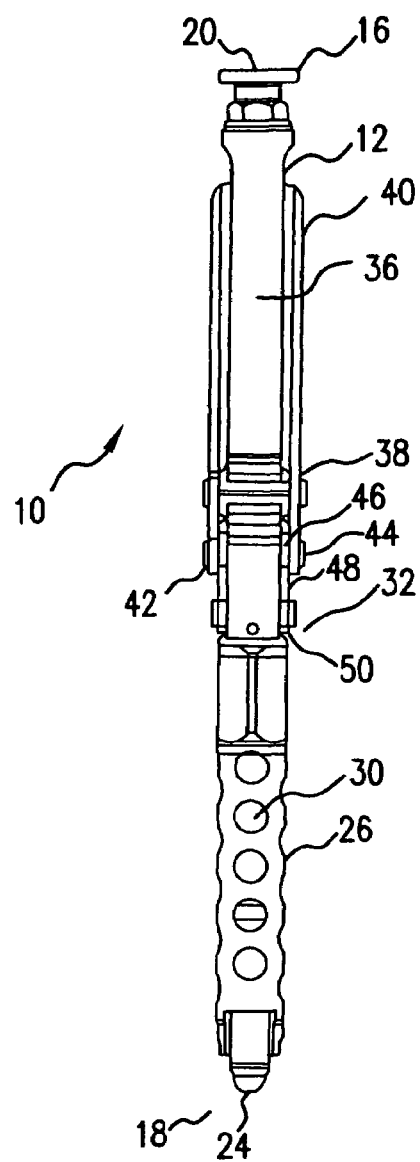
FIG. 4 shows a back view of the device shown in FIG. 3A
Figure 5:
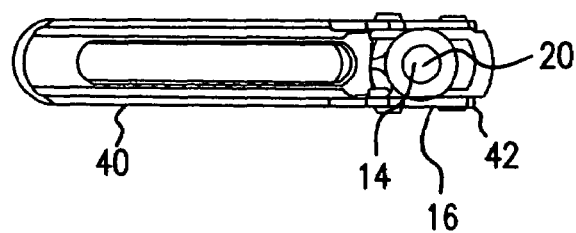
FIG. 5 shows a top view of the device shown in FIG. 3A.
Figure 7D:
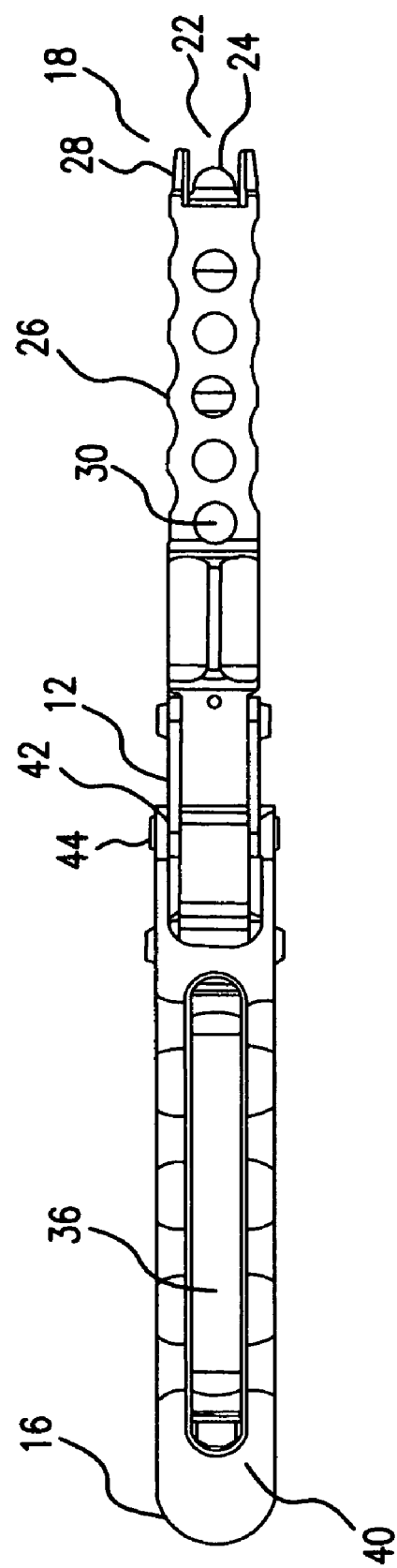

Detailed embodiments are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

FIGS. 1-8 illustrate an example of a cannulated connecting rod reducing device, generally shown at 10, which, in one simple action such as squeezing a lever, can reduce a posteriorly introduced rod into a receiving slot in the head of a bone screw and then provide an anti-torque effect to the bone screw while a bone screw locking cap introduced through the cannula of the device is secured to the bone screw.

As shown in FIGS. 1-8 the cannulated rod reducing device 10 is an elongated surgical instrument having a device housing 12 that defines a device lumen 14, which extends from the device proximal or first end 16 to the full length of device 10 exiting from the device housing 12 at the device distal or second end 18. The proximal opening 20 of the lumen 14, as defined by the first end 16 of the housing 12, is sized and configured to receive and allow free passage of a bone screw locking cap and an instrument for positioning and tightening the locking cap securely into place in the locking cap receptacle of a bone screw. The first end 16 of the device is configured to facilitate the selective, releasable attachment of an anti-torque handle, which can be of any conformation suitable to facilitate manual grasping and application of anti-torque force to the device. The lumen 14 and the exit portal 22 defined by the second end 18 of the housing 12 are similarly sized and configured to allow free passage of a bone screw locking cap and the associated tightening instrument. The housing 12 at the exit portal 22 is configured to provide bone screw grasping elements 24, which are designed to securely grasp and hold the head of a bone screw. Preferably, the grasping elements 24 are configured as a pair of opposing elements; however, other configurations for the grasping elements are within the concept of the invention.

Circumferentially and slidably disposed around a lower portion of the housing is a sleeve 26 that extends to a position proximate to the second end 18 of the housing 12. The sleeve 26 at the second end 18 of the housing 12 is configured to form a connecting rod driving member 28. The sleeve 26 can be formed with perforations 30 to reduce the overall weight of the device but must have sufficient compressive strength to be capable of transferring force applied at the proximal end of the sleeve 32. To facilitate contact with a connecting rod, the driving member 28 can be configured with a shape that is complementary to that of the connecting rod with which it will come into contact during operation. Preferably, the grasping member 28 will generally define a concavity 34; however, any shape that is complementary to the shape of the connecting rod will be within the concept of the invention.

Figure 8A:
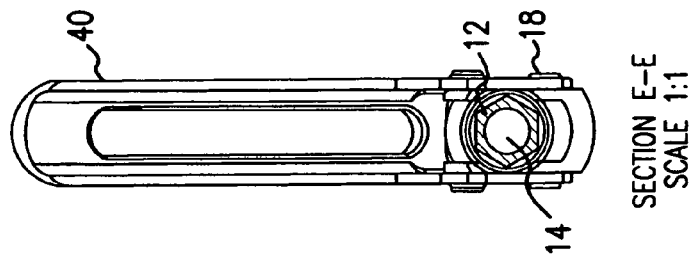
Figure 8A:
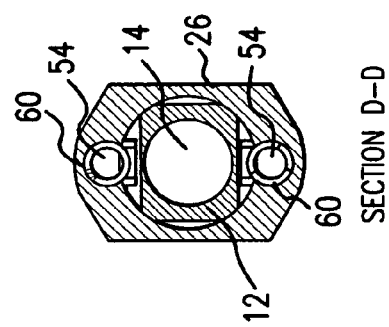
Figure 8A:
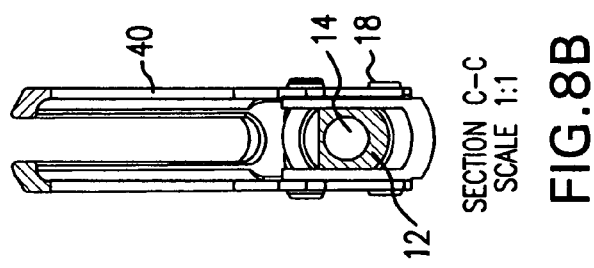
Figure 8A:
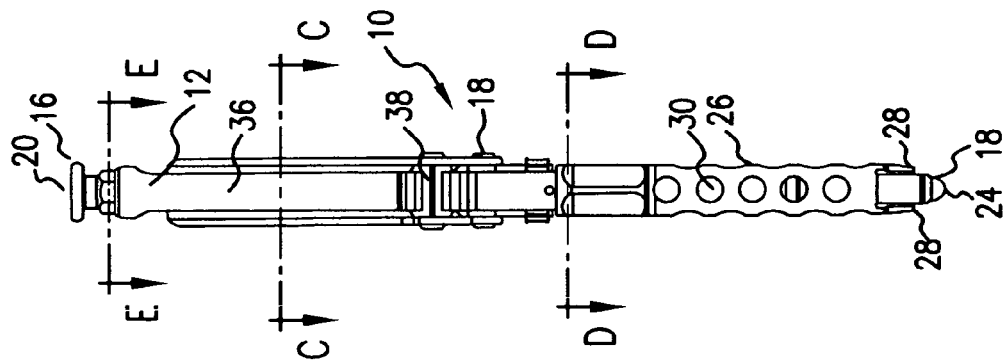

The proximal portion of the device 10 is provided with a handle 36. To facilitate operation of the device and improve the grip on the device by the user, a hand guard 38 can be provided on the housing 12 at a position above the proximal end 32 of the sleeve 26. An actuation lever 40 is pivotally mounted to housing 12 at a position above the sleeve 26 and approximately adjacent to the hand guard 38. The distal end 42 of the actuation lever 40 is pivotally connected to a second pivot point 44, which is also pivotally connected to a first end 46 of a force transfer arm 48. The second end 50 of the force transfer arm 48 is pivotally connected to the proximal end 32 of the sleeve 26. The combination of the actuation lever 40 pivotally connected to the force transfer arm 48, which in turn is pivotally connected to the sleeve 26 functions in a scissor-jack manner as is well known in the art. As shown in a comparison of FIG. 3A, the device in an open configuration, and FIG. 8A, the device in a closed configuration, the inward pivotal movement of the actuation lever 40 toward the handle 36 creates a scissor-jack transfer of force which acts to slidably move the sleeve 26 distally along the outside of the housing 12 to a position where the rod driving member 28 can contact and reduce a connecting rod into the head of a bone screw. As shown in FIGS. 1-8, the device 10 is configured to preferably reduce a connecting rod into the head of a bone screw form a position directly above the bone screw. The action of reducing the rod into the head of a bone screw is facilitated by the grasping elements 24 at the second end 18 of the housing 12 securely holding the bone screw in place relative to the device 10. As shown in FIG. 8C, the housing 12 proximate to the second end 18 and the grasping elements 24 is thickened to form a cam surface 52. As the sleeve 26 is forced distally over the cam surface 52 of the housing 12, the grasping elements 24 are forced inward so as to engage the head of a bone screw and securely hold the same.

The device can be provided with a biasing element compartment 54 that is defined as a space between a portion of the sleeve 26 and an adjacent portion of the housing 12. The compartment 54 is limited at a distal position by a biasing element stop 56 and limited at a proximal position by a retaining member stop 58. A biasing element 60 is contained within the compartment 54, the biasing element 60 is capable of compression under force and capable of expansion upon removal of the force. The biasing element 60 is preferably a coil spring and more preferably a Lee Spring that is sized to fit when fully expanded within the compartment. Within the compartment 54 and positioned above the biasing element 60 is a retaining member 62. When the actuation lever 40 is squeezed inward toward the housing 12, the pivotal action of the lever 40 and the force transfer arm 48 serves to slidably move the sleeve 26 downward along the outside of the housing 12. As the sleeve 26 moves downward, the retaining member stop 58, in contact with the retaining member 62, transfers compression force against the biasing element 60 causing it to compress against the biasing element stop 56. This compression of the biasing element 60 is only relieved when the actuation lever 40 is moved outward from the housing 12 and the relief of that compression forces serves to pull the sleeve 26 back upward along the housing and away from the second end 18 of the housing 12.

In use, a surgeon accesses the patient's spine in a known manner either using open surgical techniques or minimally invasive techniques, and prepares the bone to receive screws, as is deemed appropriate under the circumstances. Multiple screws can be inserted into bone according to the operative plan of the surgeon, and a rod is placed in or adjacent to the rod receiving recess of each respective screw. The surgeon then uses the device to position the connecting rod in the receiving portion of the head of a first screw, after which, a bone screw locking cap is positioned in the head of the bone screw through the cannula lumen 14 of the device using an appropriate instrument. The bone screw is securely held by the device 10 so as to provide an anti-torque effect as torque is applied to the locking cap by a tightening instrument inserted through the cannula lumen 14. The device 10 is then released from the screw by a reversal of the movement of the actuation lever 40. The plurality of screws can each, in turn, be attached to a connecting rod using the device 10. In the event of revision surgery, the device 10 can be used to securely hold the bone screw in place and provide anti-torque while the locking cap can be removed through the cannula lumen 14 of the device 10.

The materials used to construct the present invention are those which have sufficient strength, resiliency, and biocompatability as is well known in the art for such devices. Methods of manufacture of such surgical implant devices is also well known in the art. By way of example only, suitable materials for screw 3 include titanium, titanium alloys including Nitinol, stainless steel, and cobalt chrome alloys. The device is intended to be cleaned, re-sterilized and used in multiple procedures, and so may be made of stainless steel or other suitable materials for this purpose. Because the device is not intended to be implanted in the body, implant grade materials are not required and the additional expense for such materials may not be justified; however, such materials may be used if desired.

It is contemplated to provide the device 10 as a component of a kit that can include at least one bone screw, at least one connecting rod, at least one bone screw locking cap and the device 10. Additional devices such as cross-connectors, hooks or links can also be included in the kit.

Each of the embodiments described above are provided for illustrative purposes only and it is within the concept of the invention to include modifications and varying configurations without departing from the scope of the invention that is limited only by the claims included herewith.

What is claimed is:

1. A novel rod reducing device for use in positioning a connecting rod into position in the head of a bone screw, the device comprising:
   a housing having a first end and a second end and a lumen defined by said housing and communicating between said first end and said second end;
   a slidable sleeve having a first end and a second end, said sleeve being circumferentially disposed around at least a lower portion of said housing and terminating at said second end in a connecting rod driving member;
   a biasing element compartment containing a biasing element, said biasing element compartment defined between a portion of said sleeve and an adjacent portion of said housing;
   an actuation lever pivotally connected to said housing and operationally connected to said sleeve by a pivotal connection to a first end of a force transfer arm, which is connected at a second end to said sleeve;
   whereby the device is capable of transferring the force from said actuation lever and the force transfer arm to effect the slidable movement of the sleeve downward along the outside of the housing to a position where said connecting rod driving member is capable of contacting and forcing a rod downward into position in the head of a bone screw.

2. The device of claim 1, wherein said housing terminates in a grasping element, said grasping element configured to be capable of securely grasping the head of a bone screw when said device is activated.

3. The device of claim 2, wherein said housing further comprises at least one cam surface disposed proximate to said second end of said housing and sized to make forcible contact with said sleeve when said sleeve is slidably moved downward along the outside of said housing, said housing being bifurcated at least at the position adjacent said grasping elements such that said forcible contact between said cam surfaces of said housing and said sleeve is capable of forcing said grasping elements inward so as to be capable of securely grasping the head of a bone screw positioned there between.

4. The device of claim 3, wherein said grasping elements are configured to complement the size and shape of a groove or notch on said head of the bone screw.

5. The device of claim 3, wherein said lumen of said device is capable of acting as a cannula through which other instruments or devices can be freely passed.

6. The device of claim 5, wherein said device is capable of remaining attached to the head of a bone screw while said other instruments inserted through said lumen are used to apply torque to tighten or loosen an attachment to the head of the bone screw, the device providing an anti-torque handle attachment to facilitate an anti-torque effect on the bone screw.

7. The device of claim 1, wherein said biasing element compartment is limited at a distal position by a biasing element stop and limited at a proximal position by a retaining member stop, said biasing element capable of compression under force and capable of expansion upon removal of said force and being sized to fit when hilly expanded within said compartment, said compartment further containing a biasing element retaining member disposed between said biasing element and said retaining member stop.

8. The device of claim 7, wherein said biasing element is capable of being compressed within said compartment by the downward sliding movement of said sleeve along the outside of said housing when there is a movement of said actuation lever of the device.

9. The device of claim 1, wherein said sleeve is perforated.

10. The device of claim 1, further comprising a hand guard positioned on said housing.

11. A method of positioning and reducing a rod into the head of a bone screw, the method comprising:
   providing a rod reducing device for use in positioning a connecting rod into position in the head of a bone screw, the device comprising;
   a housing having a first end and a second end and a lumen defined by said housing and communicating between said first end and said second end;
   a slidable sleeve having a first end and a second end, said sleeve being circumferentially disposed around at least a lower portion of said housing and terminating at said second end in a connecting rod driving member;
   a biasing element compartment containing a biasing element, said biasing element compartment defined between a portion of said sleeve and an adjacent portion of said housing;
   an actuation lever pivotally connected to said housing and operationally connected to said sleeve by a pivotal connection to a first end of a force transfer arm, which is connected at a second end to said sleeve;
   whereby the device is capable of transferring the force from said actuation lever and the force transfer arm to effect the slidable movement of the sleeve downward along the outside of the housing to a position where said connecting rod driving member is capable of contacting and forcing a rod downward into position in the head of a bone screw, providing at least one bone screw and at least one connecting rod, implanting said at least one screw into the bone of a subject, positioning said device onto the head of said bone screw such that said second end of said housing is in position to grasp the head of said bone screw, actuating the device whereby said sleeve of said device is slidably moved downward along the outside of said device housing to a position where said connecting rod driving member of said sleeve contacts and forcibly reduces the rod into position in the head of the screw while the screw head is being grasped by the second end of the housing.

12. The method of claim 11, wherein the second end of the housing is provided with grasping elements which facilitate a secure grasp of the screw head.

13. The method of claim 12, wherein the actuation of the device is accomplished by the movement of an actuation lever toward the housing and said inward movement is met with resistance from the biasing element within said device.

14. The method of claim 11, further comprising the step of inserting a bone screw locking cap and tightening instrument down through the lumen of the device and tightening said locking cap into position in the head of the bone screw so as to securely lock the connecting rod into position while said device is still connected to said bone screw.

15. The method of claim 14, further comprising the step of providing an anti-torque effect for said bone screw during said tightening step.

16. The method of claim 14, further comprising the step of moving the actuation lever outward and away from the housing thereby releasing said device from the bone screw.

17. A kit for fixing bone, the kit comprising:

a rod reducing device for use in positioning a connecting rod into position in the head of a bone screw, the device comprising:

a housing having a first end and a second end and a lumen defined by said housing and communicating between said first end and said second end;

a slidable sleeve having a first end and a second end, said sleeve being circumferentially disposed around at least a lower portion of said housing and terminating at said second end in a connecting rod driving member;

a biasing element compartment containing a biasing element, said biasing element compartment defined between a portion of said sleeve and an adjacent portion of said housing;

an actuation lever pivotally connected to said housing and operationally connected to said sleeve by a pivotal connection to a first end of a force transfer arm, which is connected at a second end to said sleeve;

whereby the device is capable of transferring the force from said actuation lever and the force transfer arm to effect the slidable movement of the sleeve downward along the outside of the housing to a position where said connecting rod driving member is capable of contacting and forcing a rod downward into position in the head of a bone screw, at least one bone screw, and at least one connecting rod.

18. The kit according to claim 16, further comprising:

at least one additional tool configured to facilitate insertion or connection of a locking cap for a bone screw.

19. The device of claim 1, wherein said actuation lever is a single actuation lever pivotally connected said housing.

* * * * *